United States Patent [19]

Kato et al.

[11] Patent Number: 4,580,132
[45] Date of Patent: Apr. 1, 1986

[54] METHOD OF AND APPARATUS FOR DETECTING ELECTRICALLY CONDUCTIVE MATERIAL IN GLASS FIBERS OR ARTICLES MADE OF GLASS FIBERS

[75] Inventors: Tatsuya Kato; Toru Dogakinai, both of Fukushima, Japan

[73] Assignee: Nitto Boseki Co., Ltd., Fukushima, Japan

[21] Appl. No.: 605,683

[22] Filed: Apr. 30, 1984

[30] Foreign Application Priority Data

May 4, 1983 [JP] Japan ................... 58-78573
Sep. 22, 1983 [JP] Japan ................. 58-175750
Jan. 5, 1984 [JP] Japan ..................... 59-492

[51] Int. Cl.<sup>4</sup> ............................................ G08B 21/00
[52] U.S. Cl. ......................... 340/540; 65/158; 73/159; 73/160; 250/359.1; 340/552; 356/73.1; 356/316

[58] Field of Search .............. 340/540, 552, 568; 250/359.1; 356/316, 237, 430, 73.1; 65/29, 158; 73/159, 160

[56] References Cited

U.S. PATENT DOCUMENTS 4,161,656 7/1979 Marcuse et al. ................ 356/73.1
4,263,089 4/1981 Keller ............................ 356/316

Primary Examiner—Glen R. Swann, III
Attorney, Agent, or Firm—Bert J. Lewen; Henry Sternberg

[57] ABSTRACT

A glass fiber, strand or a product made of glass fibers is made to pass through a chamber irradiated with high-frequency radiation, so that, if the electrically conductive matters are contained, a high-frequency electric discharge occurs in the chamber accompanied by generation of light. The presence of the electrically conductive matters is made known by detecting this light by a photosensor.

11 Claims, 12 Drawing Figures

F I G. 7a
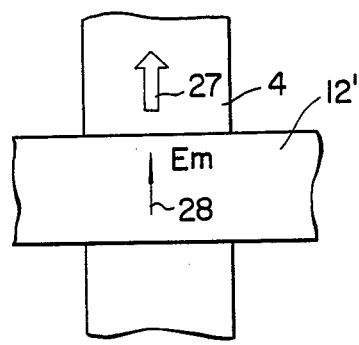
F I G. 7b
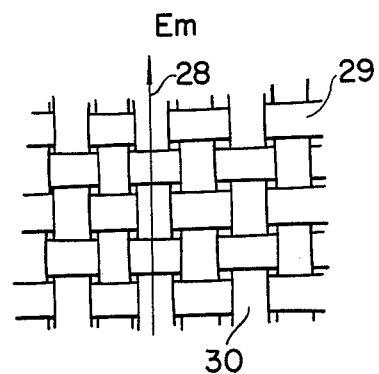

METHOD OF AND APPARATUS FOR DETECTING ELECTRICALLY CONDUCTIVE MATERIAL IN GLASS FIBERS OR ARTICLES MADE OF GLASS FIBERS

BACKGROUND OF THE INVENTION

The present invention relates to a method of detecting trace amount of electrically conductive substance which may exist in glass fibers or products made from glass fibers, as well as to an apparatus for carrying out such a method.

Glass fibers often contain foreign matter which is included in the raw materials or brought into the glass fibers during the production. Although there are many kinds of foreign matter, containment of conductive matter should be preferably avoided because such matter, even if the amounts thereof are very small, seriously impair the electric insulating power of the glass fiber products when the latter are used as insulating materials. Examples of these conductive foreign matter often found in glass fibers are metals such as gold, silver, copper and iron; metallic compounds such as nickel sulfide and iron sulfide; and alloys such as platinum-rhodium, duralumin and gun metal. Glass fiber insulating material find uses as, for example, insulation and reinforcement of printed circuit boards. In recent years, there is a trend towards higher density and quality of printed circuit boards and, accordingly, the reduction of insulating power due to containment of conductive matters in glass fibers is becoming matter of greater significance. Under this circumstance, there is an increasing demand for development of method and apparatus for detecting trace amounts of conductive matter contained in glass fibers.

Japanese Patent Laid-Open No. 61217/74 discloses a method of detecting conductive foreign matter in glass sheet. In this method, the conductive foreign matter in the glass sheet is heated by induction heating and the presence of such matter is detected through measurement of temperature rise. Unfortunately, however, this method cannot be applied satisfactorily to the detection of trace amounts of conductive foreign matter in glass fibers, because it offers only low accuracy detection.

A detecting method employing a so-called metal detector is well known. This device has a coil which forms a high-frequency magnetic field. In operation, the object to be examined is placed in this magnetic field. If the object contains some foreign matter, the magnetic field is disturbed to induce a voltage in the receiving coil, so that the presence of the conductive matter can be known by a measurement of the voltage in the receiving coil. This method, however, is effective only to find spherical metallic bodies of diameters not smaller than 100 μm, and cannot be used effectively for the detection of minute conductive matters of about 1 μm diameter contained in a single glass fiber of about 10 μm diameter of products woven from glass fibers.

SUMMARY OF THE INVENTION

Accordingly, it is an object of the invention to provide a method of and apparatus for detecting such trace amounts of conductive matter contained in glass fibers or products from glass fibers which could not be detected accurately by the prior art.

To this end, according to an aspect of the invention, there is provided a method of detecting electrically conductive matter in a glass fiber or a product from glass fibers comprising: placing the glass fiber or the product in a high-frequency electric field; and detecting the presence of the conductive matter through sensing light or sound generated as a result of a high-frequency electric discharge which is caused when the conductive matter is contained in the glass fiber or the product.

According to another aspect of the invention, there is provided an apparatus for detecting electrically conductive matter in a glass fiber or a product from glass fibers comprising: a high-frequency irradiation chamber in which high-frequency wave is irradiated; feeding means for feeding the glass fiber or the product of glass fibers through the high-frequency irradiation chamber; and a detecting means for detecting a light or sound produced in the high-frequency irradiation chamber.

According to the invention, the glass fiber to be examined is made to run through a high-frequency electric field of a frequency preferably ranging from several MHz to several thousands of MHz, a power preferably ranging from several hundreds of watts to several tens of KW, and an intensity of electric field of several thousands to several tens of thousands of (v/m). When the portion of the glass fiber containing conductive matter enters the high-frequency electric field, this portion of the glass fiber instantaneously produces a sparking light and, at the same time, a sound. The light and the sound are produced very accurately in response to the presence of the conductive matter, even when the size of the conductive matter is very small, e.g. of a diameter less than 1 μm in a single glass fiber and of about 10 μm diameter in a product woven from such glass fibers. The time lag of the production of the light and the sound after the entry of the glass fiber portion into the electric field is negligibly small so that the detection can be made at a high accuracy even if the detecting operation is conducted at a high speed. The light or sound thus produced is detected by an ordinary photosensor or sound wave detector output signal which is sent to a suitable processing circuit. With such an arrangement, it is possible to detect even a trace amount of conductive matter existing in glass fibers.

The object which is subjected to the detecting method and apparatus of the invention may be either the glass fiber itself or products from glass fibers. Various forms of glass fibers such as a mono-filament, a strand, or a roving and can be examined by the method and apparatus of the invention. Examples of the products from glass fibers, suitable for examination by the method and apparatus of the invention, are fabrics woven from glass fibers, cloth knitted from glass fibers, non-woven fabric of glass fibers, glass fiber papers, glass fiber mats and the like.

The condition of the high-frequency electric field preferably fall within the ranges mentioned above. Conditions far from these ranges will undesirably impair the sensing accuracy.

The light or sound issued from the glass fiber portion containing the conductive matter within the high-frequency electric field are of levels which can be picked up by ordinary sensors and sound wave detectors. Preferably, the photosensor used in the method of the invention is sensitive only to selected wavelengths. The signal produced as a result of the detection may be used for activating a circuit such as a printing circuit, an alarm circuit or an emergency stop circuit.

In the method and apparatus of the invention, the strength of the electric discharge of the conductive matter is maximized when the conductive matter lies parallel with the direction of the electric field, and is minimized when the same lies perpendicular to the direction of the electric field. Therefore, the detection of conductive matters in a mono-filament, a strand or a roving can be conducted without substantial difficulty because it is easy to keep the conductive matter in parallel with the direction of the electric field. In the case of products of glass fibers such as fabric woven from glass fibers, cloth knitted from glass fibers and so forth, some conductive matter may not lie in parallel with the direction of the electric field, so that the electric discharge may be weakened and hinder the detection. Particularly, in the case of a product woven from glass fibers, the conductive matter in, for example, the weft are always laid perpendicularly to the direction of the electric field and, hence, can hardly be detected.

Accordingly, the invention has as another object a method of and apparatus for detecting conductive matters in products from glass fibers, improved to permit effective detection regardless of the orientation of the conductive matter in the product.

To this end, the invention provides a detecting method and apparatus in which the product of glass fibers to be examined is made to pass through a high-frequency irradiation chamber of wave-guide type, while forming an electric field in the high-frequency irradiation chamber at an inclination to the direction of feed of the product.

Other objects, features and advantages of the invention will become clear from the following description of the preferred embodiments taken in conjunction with the accompanying drawings.

BRIEF DESCRIPTION OF THE DRAWINGS

FIG. 6b shows the electric field pattern in the high-frequency irradiation chamber shown in FIG. 6a;

FIG. 7a is an illustration of the direction of feed of the object and the direction of the electric field in the high-frequency irradiation chamber of the embodiment shown in FIG. 6a;

FIG. 7b shows the relationship between the direction of electric field and weft and warp of the object in the high-frequency irradiation chamber shown in FIG. 6a;

FIG. 8b is an illustration showing the relationship between the direction of electric field and the weft and warp of the object in the embodiment shown in FIG. 8a; and FIG. 9 is a schematic plan view of a modification of the apparatus shown in FIG. 8a.

DESCRIPTION OF THE PREFERRED EMBODIMENTS

Figure 1:
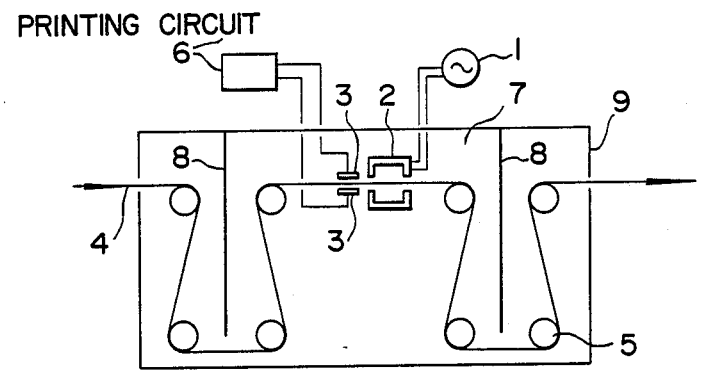
FIG. 1 is a schematic illustration of an embodiment of the invention.

An embodiment of the invention will be described hereinunder with reference to FIG. 1. A high-frequency electric field forming section 2 of the box-oven type is connected to a high-frequency power source 1 and is disposed in a dark room 7 formed between two partition walls 8 within a casing 9. A plurality of guide rollers 5 are mounted in the casing 9 to define a zig-zag path along which a fabric 4 woven from glass fibers to be examined is fed as indicated by arrows, passing though the high frequency electric field forming section 2 in the dark room 7. A photosensor 3 is disposed in the dark room 7 so as to be opposed to the inlet to the high-frequency electric field forming section 2. The photosensor 3 is connected to a printing circuit 6 disposed outside the casing 9.

Figure 2:
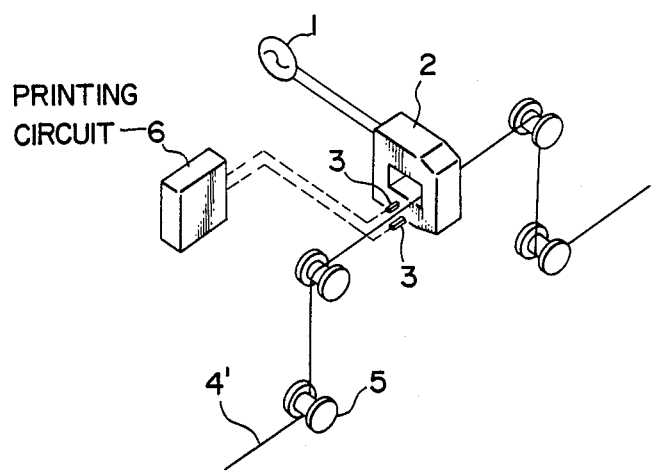
FIG. 2 is a perspective view of a modification of the embodiment shown in FIG. 1, modified for application to the examination of a glass fiber strand.

If the fabric 4 of the glass fibers contains conductive matter, an electric discharge is caused accompanied by light and sound as the portion of the fabric 4 containing the conductive matter enters the high-frequency electric field forming section 2. The light thus generated is detected by the photosensor 3 the output of which is delivered to the printing circuit 6 which indicates the presence of the conductive matter. The same effect can be obtained by substituting an acoustic detector for the photosensor 3. The output from the photosensor 3 may be delivered to other circuit than the printing circuit, such as an alarm circuit, fabric feed emergency stop circuit and so forth. FIG. 2 shows a modification in which the high-frequency electric field forming section 2 and the guide rollers 5 are shaped and sized to suit to the examination of a glass fiber strand 4'.

Practical examples of operation of the detecting apparatus described hereinabove will be explained hereinunder.

EXAMPLE 1

A silver-glass composite glass filament was prepared to have a continuous glass filament of 9 μm dia. and a continuous silver line of 3 μm dia. along the axis of the glass filament. This composite glass filament was used as a specimen of the glass fiber containing a conductive matter. The specimen was cut into pieces of 2 mm long. A fabric was woven from glass fiber strands each consisting of 400 glass filaments of 9 μm dia, at the density of 44 warp strands per inch and 34 weft strands per inch. 100 pieces of the specimen mentioned above were dispersed in the fabric in such a manner so as not to drop from the fabric. The fabric 4 containing conductive matter was made to pass at a velocity of 40 m/min through the high-frequency electric field forming section 2 of the apparatus shown in FIG. 1. The frequency, power and the intensity of the electric field were 2450 MHz, 1 Kw and 6 kilo(v/m), respectively. Throughout the period of running of the fabric, the photosensor 3 operated 100 times.

EXAMPLE 2

The same operation as Example 1 was conducted using the same glass fibers containing conductive matter as that used in Example 1 except that copper was used in place of silver as the conductive matter. The photosensor operated 100 times during the period of running of the fabric.

EXAMPLE 3

The same specimen of the glass fiber containing conductive matter as that used in Example 1 was cut into pieces of 2 mm long. Also prepared was a glass strand consisting of 400 glass filaments of 9 $\mu$m dia. and specified as ECG 75 -/OZ in Japanese Industrial Standard. 100 pieces of the cut specimen mentioned above were dispersed in the glass fiber strand at a pitch of about 1 m in the lengthwise direction of the strand so as not to drop from the strand. The glass fiber strand was made to pass at a velocity of 150 m/min through the high-frequency electric field forming section 2 of the apparatus as shown in FIG. 2. The frequency, power and intensity of the electric field were 2450 MHz, 1 Kw and 6 kilo(v/m), respectively. 100 times of operation of the photosensor 3 were confirmed also in this case.

Figure 3:
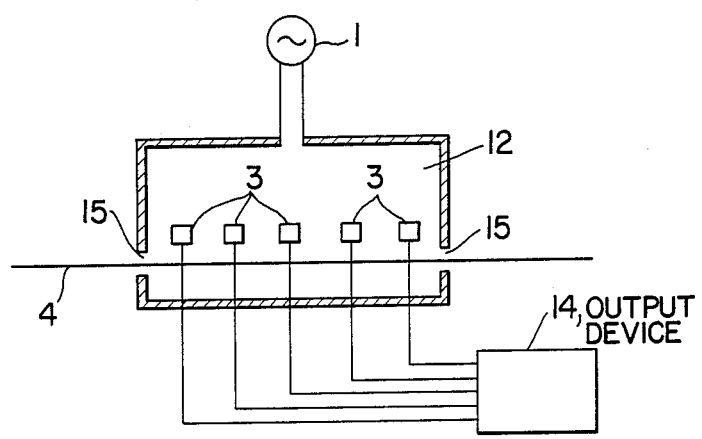
FIG. 3 is a schematic illustration of another embodiment of the invention employing a high-frequency irradiation chamber of the box-oven type.

FIG. 3 shows another embodiment in which a high-frequency irradiation chamber defining a dark room therein was used as the high-frequency electric field forming section 2 of the embodiment shown in FIG. 1. The high-frequency power source 1 of the embodiment shown in FIG. 3 may be an ordinary high-frequency oscillator which can produce high-frequency wave of frequencies ranging between several MHz and several thousands of MHz and powers ranging between several hundreds of W and several tens of KW. When frequency higher than 10 MHz is required, high-frequency waves having frequencies as specified in "Frequencies for Industrial, Scientific and Medical Uses" (Abbreviated as "ISM band") are used preferably. The high-frequency irradiation chamber 12 is of a box-oven type and constitutes a space for irradiating the object with the high-frequency wave generated by the high-frequency oscillator 1. In operation, the object 4 to be examined is fed by a feed roll (not shown) and is introduced into the high-frequency irradiation chamber 12 through a slit 15 formed in the left wall of the chamber 12 and, after irradiation with the high-frequency wave, comes out of the chamber 12 through a slit 15 formed in the right wall of the chamber 12. The object 4 is then taken up by a take-up roll which is not shown. The slit 15 permits the introduction of the object 4 into the high-frequency irradiation chamber 12. The size of the slit 15, therefore, should be selected to allow the introduction of the object 4 into the high-frequency irradiation chamber 12. Taking into account the prevention of leak of high-frequency wave, however, the breadth of the slit is preferably selected to be not greater than 25 mm when the frequency is 2450 MHz.

As stated before, spark like light is produced accompanied by sound when the portion of the object containing conductive matter is brought into the high-frequency irradiation chamber 12. The light thus generated is detected by the photosensor 3 sensitive to the light. The sensor 3 may of of any desired type, provided that it can detect the light, e.g. a photoelectron multiplier tube, phototransistor and photodiode.

Upon sensing the light, the sensor 3 produces a signal which is used as the input signal to a suitable output device 14 used in the production process, such as an alarm buzzer, marking device and emergency stopper. The sensor 3 may be installed at any desired position suitable for the sensing of the light.

Figure 4:
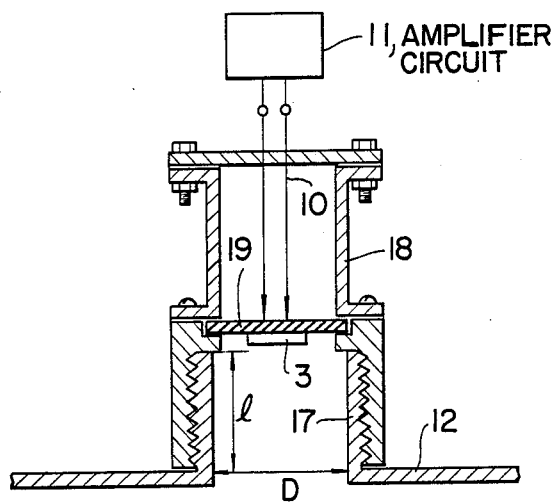
FIG. 4. is a sectional view showing the detail of a preferred example of construction of a detector incorporated in the embodiment shown in FIG. 3.

In the embodiment shown in FIG. 3, five sensors 3 are disposed on the side wall defining the high-frequency irradiation chamber 12. More specifically, referring to FIG. 4 showing a section of the apparatus shown in FIG. 3 near the sensor 3, cylindrical recesses 17, each having a diameter of D mm and depth of 1 mm are formed in the wall of the high-frequency wave irradiation chamber 12 and a photodiode as the sensor 3 is placed on the bottom of each cylindrical recess 17. With this arrangement, it is possible to prevent the high-frequency wave from affecting the sensors 3. It is also possible to shield the photodiode by a magnetically shielding material such as permalloy (NiFe alloy), in order to prevent any disturbance. The signal produced by the sensor 3 (photodiode) upon sensing the light is delivered to an external amplifier circuit 11 through a lead line 10 extended through an insulating plate 19 and the wall of a container 18.

Figure 5:
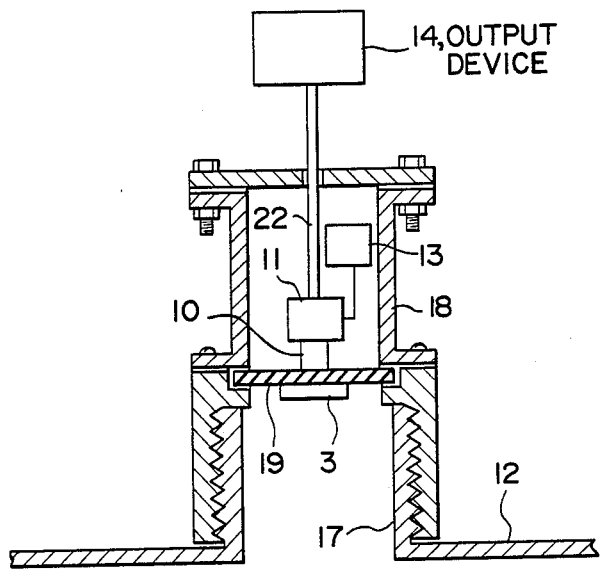
FIG. 5 is a sectional view of a modification of the construction as shown in FIG. 4.

FIG. 5 shows another arrangement in which the sensors 3 are disposed in the bottoms of the recesses 17 formed in the wall of the high-frequency irradiation chamber 12 as in the case of FIG. 4. In this arrangement, however, the amplifier circuit 11 for amplifying the output signal of the sensor 3 is disposed in the vicinity of the sensor 3 across the insulating plate 19 so that the length of the lead line 10 is much decreased. In addition, the output from the amplifier circuit 11 is transmitted to the device 14 such as alarm device, marking device or emergency stopper through an optic glass fiber 22. With this arrangement, it is possible to prevent any electric and magnetic hindrance in the signal transmission. A reference numeral 13 designates a power source for amplifier circuit 11, normally batteries.

The present inventors have conducted a test under the following conditions (a) to (g), using the apparatus shown in FIG. 3.

(a) Conductive matter

A continuous line of silver having a diameter of 3 $\mu$m in the core portion of a single glass filament of 9 $\mu$m dia, the glass filament and the silver line in combination constituting a silver-glass composite glass filament.

(b) Object

A fabric woven from glass fiber strands each consisting of 400 filaments of 9 $\mu$m dia, at density of 44 warp threads per inch and 34 weft threads per inch. The above-mentioned silver-glass composite glass filament was cut into pieces of 2 mm long and 100 of such pieces were dispersed in the woven fabric at a lengthwide pitch of 1 m so as not to come off from the fabric.

(c) High-frequency oscillator

Frequency 2450 MHz and output 600 w.

(d) Form and size of high-frequency irradiation chamber

Box-shape of 200 mm high, 330 mm wide and 200 mm long.

(e) Form and size of slit

Rectangular form of 20 mm high and 270 mm wide.

(f) Sensor

Photodiode (S 1723-02, manufactured by Hamamatsu Photonics)

(g) Velocity of run through high-frequency irradiation chamber 80 m/min

The light produced in the high-frequency irradiation chamber 12 was sensed by the sensor 3 which in turn produced a signal for activating a piezoelectric buzzer. The test resulted in the operation of the buzzer 100 times.

Further tests were conducted by using nickel sulfide and copper in place of silver, respectively, under the same condition as described above. Operation of the piezoelectric buzzer 100 times was confirmed also in each case. Similar tests were conducted by using, as the examination object, a glass strand consisting of 400 filaments each of 9 μm dia. (JIS ECG 75-1/01Z) in place of the woven fabric. The test conditions were same as those described before, except that the rectangular slit was substituted by a circular hole of 10 mm dia. and that the running speed of the object through the high-frequency irradiation chamber 2 was increased to 150 m/min. Operation of the piezoelectric buzzer 100 times was confirmed also in this case.

Figure 6A:
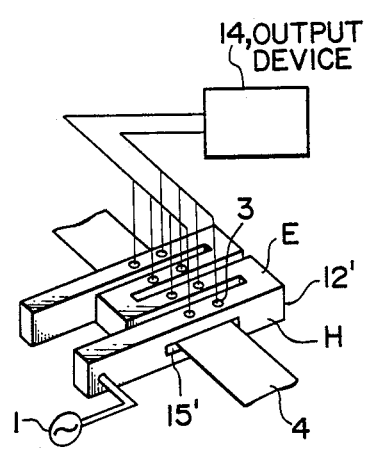
FIG. 6a is a perspective view of an embodiment of the invention making use of a high-frequency irradiation chamber of the wave-guide type.
Figure 6B:
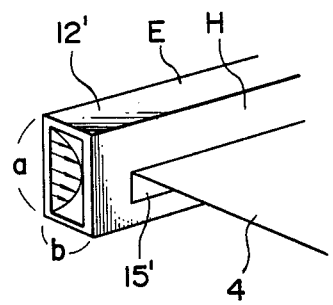

FIGS. 6a and 6b show ahother embodiment of the invention employing a high-frequency irradiation chamber of waveguide tube type. In this embodiment, a microwave oscillator using a magnetron is used as the high-frequency oscillator 1. More specifically, a rectangular wave-guide tube is folded in a multiplicity of stages to form a high-frequency irradiation chamber 12', and a slot 15' is formed in the center of the wider surfaces H, while narrower surfaces E carry sensors 3. The power from the high-frequency oscillator 1 of microwave band is transmitted through the wave-guide tube to the high-frequency irradiation chamber 12'. According to this arrangement, the relationship between the maximum value of the electric field in the high-frequency irradiation chamber 12' and the transmitted power is given by the following formula (1)

$$\frac{P}{ab} = K\sqrt{1 - (fc/f)^2} \, |Emax|^2 \tag{1}$$

where, p represents the transmitted power, a represents the length of longer axis of the wave-guide tube, b represents the length of the shorter axis of wave-guide tube, fc represents the cut-off frequency which is determined by the transmission mode, f represents the operation frequency, Emax represents the maximum value of the electric field in the high-frequency irradiation chamber and K represents a constant. The maximum value of the electric field in the high-frequency irradiation chamber 12' can be selected as desired by adjusting the level of the transmitted microwave power. It will be seen that a highly efficient sensing can be performed in the illustrated arrangement because the maximum value Emax of the electric field resides in the area where the object 4 passes.

In the arrangement shown in FIGS. 6a and 6b, the object 4 runs in the direction 27 parallel to the direction 28 of the electric field in the high-frequency irradiation chamber 12', as will be seen from FIG. 7a. The generation of the spark-like light is generated when the minute conductive matter is placed in the direction parallel to the direction 28 of the electric field in the high-frequency irradiation chamber 12'. Namely, the detection of the conductive matter can be conducted without substantial difficulty if the object has a fibrous form such as a mono-filament, a strand, a roving or the like because, in such a case, the orientation of the conductive matter can easily be maintained in parallel with the direction 28 of the electric field in the high-frequency irradiation chamber 12'. In the case where the object is a product of glass fibers such as fabric woven from glass fibers, cloth knitted from glass fibers or the like, as shown in FIG. 7b the detection of the conductive matter encounters the following difficulty. Firstly, since the object is constituted by weft 29 and warp 30, the weft 29 are always maintained perpendicular to the direction 28 of the electric field in the high-frequency irradiation chamber, so that the minute conductive matter existing in the weft 29 can hardly be detected. Secondly, if the object contains conductive matter oriented in various directions, the apparatus described hereinbefore, having unidirectional electric field, cannot effectively detect the conductive matter perpendicular to the direction of the electric field, although it can provide a high intensity electric field. This fact is proved also by the following formula worked out by the present inventors.

$$Em = K.1/l \tag{2}$$

Em: electric field intensity necessary for the detection of conductive matter
l: length of conductive matter parallel to Em
K: constant Thus, the intensity of the electric field in the high-frequency irradiation chamber, provided that the electric field is parallel to the conductive matter, is in inverse proportion to the length of the conductive matter. For instance, in order to examine a copper-glass composite glass filament containing a copper piece of 1 mm long and 1 μm dia. by means of the apparatus shown in FIG. 6a, the electric field intensity required for the detection of the copper when the composite glass filament is placed perpendicularly to the direction of electric field is about 1000 times as large as that required for the detection of copper when the composite glass filament is placed in parallel to the direction of electric field. With the apparatus shown in FIG. 6a, therefore, it has been difficult to detect the conductive matter existing in the weft of the products of glass fibers such as fabric woven from glass fibers, cloth knitted from glass fibers and so forth.

Thus, the apparatus having the wave-guide tube type high-frequency irradiation chamber as shown in FIG. 6a encounters a problem concerning the directivity of the detection characteristics, due to the unidirectional orientation of the electric field. In contrast, the apparatus using the oven-type high-frequency irradiating chamber is free from this problem because it has a multiplicity of orientation of electric field in the high-frequency irradiation chamber. In this case, however, it is not possible to obtain a high electric field intensity and, accordingly, the conductive matter smaller than a predetermined size cannot be detected accurately.

Figure 8A:
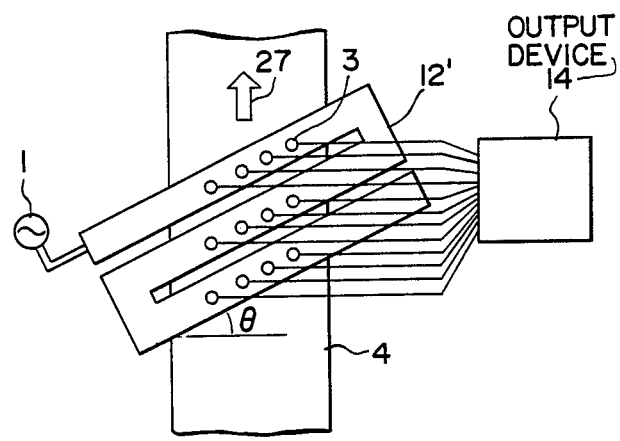
FIG. 8a is a schematic plan view of an embodiment of the invention suitable for use in the case where the object includes glass fibers the direction of which does not coincide with the direction of electric field in the high-frequency irradiation chamber.
Figure 9:
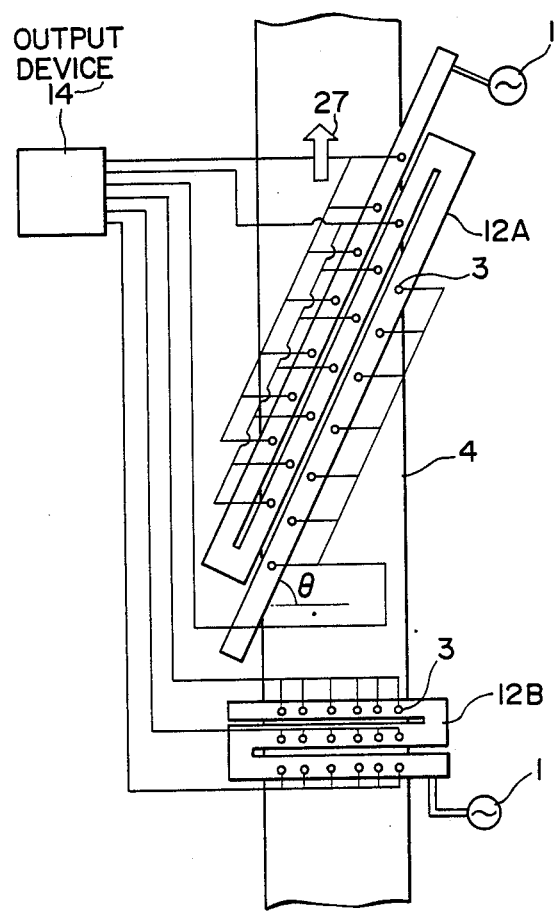

FIGS. 8a and 9 show embodiments which can effectively be used in the detection of minute conductive matter which require specifically high electric field for the detection, in the glass fiber products such as woven fabric, knitted cloth and non-woven fabric of glass fibers containing much conductive matter in indefinite orientations.

Figure 8B:
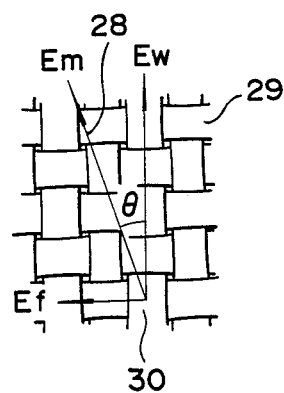

More specifically, in the embodiment shown in FIG. 8a, the high-frequency irradiation chamber 12' is inclined at an angle θ to the direction 27 of movement of the object 4. Assuming here that the object 4 is a fabric woven from glass fibers, the electric field acts on the weft 29 and warp 30 of the fabric 4 in a manner shown in FIG. 8b. Namely, the electric field intensity Em in the high-frequency irradiation chamber is divided into a component Ef parallel to the wefts 29 of the object and a component Ew parallel to the warps 30 of the same, so that both of the weft 29 and warp 30 always pass through an electric field parallel thereto. The components Ef and Ew of the electric field intensity Em in the high-frequency irradiation chamber are given by the following formulae.

$$Ef = Em \sin \theta \quad (3)$$

$$Ew = Em \cos \theta \quad (4)$$

As will be theoretically understood from formula (3), the electric field intensity component Ef exists unless the angle $\theta$ is zero. For obtaining a practically acceptable accuracy of detection, however, the angle $\theta$ is preferably selected not to be smaller than 10°. By using the apparatus shown in FIG. 8a, it is possible to generate the spark-like light from the conductive matter, in whichever one of the weft and warp the conductive substance may exist. The light thus generated is detected by the photosensor 3 sensitive to the light. The sensor 3 may be of any desired type, provided that it can detect the light, e.g. a photoelectron multiplier tube, a phototransistor or a photodiode.

Upon sensing the light, the sensor 3 produces a signal which is used as the input signal to a suitable device 14 used in the production process, such as an alarm buzzer, marking device and emergency stopper. The sensor 3 may be installed at any desired position suitable for the sensing of the light. In the embodiment shown in FIG. 8a, twelve sensors 3 are disposed on the upper wall defining the high-frequency irradiation chamber 12'.

In the case where the possibility of the conductive matter in the weft or warp is unknown, it is desirable that the arrangement is made to equalize Ef and Ew given by the formulae (3) and (4). In such a case, therefore, the angle $\theta$ should be selected to be 45°. The inclination of the high-frequency irradiation chamber 12' by $\theta$ causes a reduction of the electric field intensity component Ew parallel to the warps 30 by an amount $\cos \theta$ as compared with the case where the chamber is not inclined, i.e. as compared with the case of $\theta = 0$ and $Ew = Em$. The electric field intensity component Em is given by the following formula.

$$Em = 2 \times \sqrt{\frac{2p}{a \times b}} \, 2 = \sqrt{\frac{\frac{\mu}{\epsilon}}{1 - \left(\frac{\lambda}{\lambda_c}\right)^2}} \quad (5)$$

where, a represents the longer axis length of the wave-guide tube, b represents the sorter axis length of the wave-guide tube, p represents the output power of the high-frequency oscillator, $\lambda$ represents the wave-length in free space and $\lambda_c$ represents the cut-off wave-length.

It is, therefore, possible to compensate for the reduction of the electric field intensity component Ew by decreasing the size (a×b) of the wave-guide tube and/or increasing the power P of the high-frequency oscillator.

The present inventors have conducted a test under the following conditions (a) to (g), using the apparatus shown in FIG. 8.

(a) Conductive matter

A continuous line of silver having a diameter of 3 $\mu$m in the core portion of a single glass filament of 9 $\mu$m dia, the glass filament and the silver line in combination constituting a silver-glass composite glass filament.

(b) Object

A fabric woven from glass fiber strands each consisting of 400 filaments of 9 $\mu$m dia, at density of 44 warp threads per inch and 34 weft threads per inch. The above-mentioned silver-glass composite glass filament was cut into pieces of 2 mm long and 100 of such pieces were dispersed in the weft and 100 pieces in the warp at random pitch so as not to come off from the fabric.

(c) High-frequency oscillator

Frequency 2450 MHz and output 600 w.

(d) Sensor

Photodiode (S 1723-02 manufactured by Hamamatsu Photonics)

(e) Velocity of run through high-frequency irradiation chamber 80 m/min (f) Form and size of slits Rectangular slits of 16 mm high and 320 mm wide.

The light thus generated in the high-frequency irradiation chamber 12' were sensed by the sensor 3 and a counter was activated by the output signals from the sensor 3 to measure the number of operations of the sensor 3. As a result, the counter counted 200 operations.

Similar tests were conducted under the same conditions as above, but using nickel sulfide and copper as the conductive matter in place of silver. The counter counted 200 operations in each case.

It will be understood that the described embodiment permits the detection of all conductive matter contained by the warp and weft of the flat fabric woven from glass fibers. However, in the case where the conductive matter exist in the product of the glass fibers in a random orientation and some of the conductive matter exist in the direction perpendicular to the direction of the electric field, the detection of such conductive matter will fail undesirably.

FIG. 9 shows a further embodiment of the invention in which two high-frequency irradiation chambers are provided to detect the conductive matter regardless of the orientation of the conductive matter. More specifically, this embodiment has a high-frequency irradiation chamber 12A for weft and a high-frequency irradiation chamber 12B for warp. In the high-frequency irradiation chamber 12A for weft, the electric field is inclined with respect to the direction 27 of movement of the object 4 at an angle greater than 45° and approximating as much as possible 90° without imparing the passage of the object through the slit. On the other hand, in the high-frequency irradiation chamber 12B for warp, the inclination of the electric field to the direction of movement of the object 4 is zero. The intensities of electric field applied weft and warp in to the high-frequency irradiation chambers 12A and 12B are given by the following formulae, respectively.

$$E_{fA} = E_{mA} \sin \theta \; (\theta > 45°) \quad (6)$$

$$E_{wA} = E_{mA} \cos \theta \quad (\theta > 45°) \tag{7}$$

where, $E_{mA}$ represents the high-frequency electric field intensity in the high-frequency irradiation chamber 12A, $E_{fA}$ represents the component of electric field intensity applied to the weft in the high-frequency irraditon chamber 12A, and $E_{wA}$ represents the component of electric field intensity applied to the warp in the high-frequency irradiation chamber 12A.

$$E_{fB} = 0 \tag{8}$$

$$E_{wB} = E_{mB} \tag{9}$$

where, $E_{mB}$ represents the high-frequency electric field intensity in the high-frequency irradiation chamber 12B, $E_{fB}$ represents the component of electric field intensity applied to the weft in the high-frequency irradiation chamber 12B, and $E_{wB}$ represents the component of electric field intensity applied to the warp in the high-frequency irradiation chamber 12B.

As will be realized from these formulae, the component $E_{fA}$ of electric field intensity applied to the weft in the high-frequency irradiation chamber 12A is greater than that given by the formula (3) mentioned before. This means that the detection of conductive matter contained in the weft of the object 4 is further facilitated as compared with the embodiment shown in FIG. 8a. On the other hand, as will be seen from formula (9), the intensity component $E_{wB}$ of the electric field applied to the warp in the high-frequency irradiation chamber 12B is equal to the electric field intensity $E_{mB}$ in the high-frequency irradiation chamber 12B. This means that also the detection of the conductive matter is facilitated as compared with the embodiment shown in FIG. 8b.

To equalize the electric field intensity components applied to the weft and warp of the object, the following condition derived from formulae (6) and (9) should be met.

$$E_{mA} \sin \theta = E_{mB} \tag{10}$$

This can be achieved by adjusting the electric field intensities in the high-frequency irradiation chambers 12A and 12B by using the condition as expressed by the formula (5) mentioned before. To this end, the embodiment shown in FIG. 9 has high-frequency oscillators for respective high-frequency wave irradiation chambers.

When the condition of formula (10) is not necessary, the embodiment shown in FIG. 9 may be modified such that the high-frequency irradiation chambers 12A and 12B are coupled to each other through a wave-guide tube which suffers from only small loss of energy and which does not cause large change of the high-frequency mode, while eliminating one of the high-frequency oscillators.

In the explained hereinabove with reference to FIG. 9, the conductive matter which could never be detected in one of the high-frequency irradiation chambers can be detected without fail in the other high-freqeuncy irradiation chamber. This embodiment, therefore, can suitably be applied to the detection of conductive matters not only in the glass fiber products in which the warp and weft are arranged to intersect at a right angle but also in the cloth knitted from glass fibers, non-woven glass fiber fabric, glass fiber paper, glass fiber mat and so forth in which the glass fibers are arranged in a random direction.

As will be fully understood from te foregoing description, the method and apparatus for detecting electrically conductive matter in accordance with the invention permit a quick and accurate detection of even a trace amount of conductive matter residing in the glass fiber. In consequence, in the production of glass fiber products used as the insulating and reinforcement members for printed circuit boards which require specifically high insulating power, it is possible to easily detect and reject the product which contain conductive matter, thereby to enable the manufacture to forward only the acceptable goods devoid of conductive matter which would impair the insulating power.

Although the invention has been described in specific terms, it will be understood by those skilled in the art that the described embodiments are only illustrative. For instance, when it is not necessary to use the high-frequency oscillator having oscillation frequency of 2450 MHz and if the method needs not be incorporated in the process for producing the products, the presence of conductive matter in glass fibers can be detected easily by means of a microwave oven for household use.

Other changes and modifications are possible without departing from the scope of the invention which is limited solely by the appended claims.

What is claimed is:

1. A method of detecting electrically conductive matter in a glass fiber or a product made from glass fibers comprising: placing said glass fiber or said product in a high-frequency electric field; and detecting the presence of said conductive matter through sensing light or sound generated as a result of a high-frequency electric discharge which is caused when said conductive matter is contained in said glass fiber or said product.

2. A method of detecting electrically conductive matter according to claim 1 comprising: providing a high-frequency irradiation chamber of wave-guide tube type adapted to produce said high-frequency electric field; feeding said product through said high-frequency irradiation chamber; and inclining the direction of the electric field is said high-frequency irradiation chamber with respect to the direction of feed of said product.

3. A method of detecting electrically conductive matter according to claim 2, further comprising: feeding said product through a second high-frequency irradiation chamber of wave-guide tube type in which an electric field in a direction different from that in the first said high-frequency irradiation chamber is produced; and sensing the light or sound generated in said second high-frequency irradiation chamber.

4. An apparatus for detecting electrically conductive matter in a glass fiber or a product from glass fibers comprising: a high-frequency irradiation chamber into which high-frequency radiation is irradiated; feeding means for feeding said glass fiber or product through said high-frequency irradiation chamber to be examined; and a detecting means for detecting a light or sound produced in said high-frequency irradiation chamber.

5. An apparatus for detecting electrically conductive matter according to claim 4, wherein said high-frequency irradiation chamber is of a box-type oven construction.

6. An apparatus for detecting electrically conductive matter according to claim 4, wherein said high-frequency irradiation chamber is of a wave-guide tube type construction.

7. An apparatus for detecting electrically conductive matter according to claim 6, wherein said high-frequency irradiation chamber is so arranged that the direction of the electric field formed therein is inclined to the direction of feed of said product.

8. An apparatus for detecting electrically conductive matter according to claim 7, further comprising: a second high-frequency irradiation chamber of wave-guide tube type construction adapted to form an electric field in a direction different from that of the electric field in the first-mentioned high-frequency irradiation chamber, said product of glass fiber being adapted to pass through said second high-frequency irradiation chamber; and a detecting means for detecting light or sound produced in said second high-frequency irradiation chamber.

9. An apparatus for detecting electrically conductive matter according to any one of claims 4 to 8, wherein the output from said detecting means is delivered to an alarm device, marking device or emergency stop device, through an amplifier circuit.

10. An apparatus for detecting electrically conductive matter according to any one of claims 4 to 8, wherein said detecting means includes a sensor disposed on the bottom of a recess formed in a wall defining said high-frequency irradiation chamber and adapted to detect the light produced in said high-frequency irradiation chamber.

11. An apparatus for detecting electrically conductive matter according to any one of claims 4 to 8, wherein said detecting means includes a sensor disposed on the bottom of a recess formed in a wall defining said high-frequency irradiation chamber and adapted to detect the light produced in said high-frequency irradiation chamber, said apparatus further comprising: an amplifier circuit disposed outside said recess and in the vicinity of said sensor and adapted to amplify the output of said sensor; and an optic fiber through which the output from said amplifier circuit is delivered to an alarm device, marking device or emergency stop device.

* * * * *